United States Patent
Sun et al.

(10) Patent No.: US 12,161,499 B2
(45) Date of Patent: Dec. 10, 2024

(54) SYSTEMS AND METHODS FOR FOUR-DIMENSIONAL CT SCAN

(71) Applicant: SHANGHAI UNITED IMAGING HEALTHCARE CO., LTD., Shanghai (CN)

(72) Inventors: Buliang Sun, Shanghai (CN); Wei Zhang, Shanghai (CN); Jonathan Maltz, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 573 days.

(21) Appl. No.: 17/446,468

(22) Filed: Aug. 31, 2021

(65) Prior Publication Data

US 2021/0386392 A1 Dec. 16, 2021

Related U.S. Application Data

(63) Continuation of application No. PCT/CN2019/102719, filed on Aug. 27, 2019.

(51) Int. Cl.
*A61B 6/00* (2024.01)
*A61B 6/02* (2006.01)
*A61B 6/03* (2006.01)
*A61B 6/46* (2024.01)

(52) U.S. Cl.
CPC ............ *A61B 6/5229* (2013.01); *A61B 6/027* (2013.01); *A61B 6/035* (2013.01); *A61B 6/469* (2013.01); *A61B 6/54* (2013.01); *A61B 6/563* (2013.01)

(58) Field of Classification Search
None
See application file for complete search history.

(56) References Cited

U.S. PATENT DOCUMENTS

| 4,965,726 A | 10/1990 | Heuscher et al. |
| 2004/0081270 A1* | 4/2004 | Heuscher ............... A61B 6/027 378/4 |

(Continued)

FOREIGN PATENT DOCUMENTS

| CN | 101004764 A | 7/2007 |
| CN | 105615912 A | 6/2016 |

(Continued)

OTHER PUBLICATIONS

International Search Report in PCT/CN2019/102719 mailed on May 29, 2020, 5 pages.

(Continued)

*Primary Examiner* — Edwin C Gunberg
(74) *Attorney, Agent, or Firm* — METIS IP LLC

(57) ABSTRACT

Systems and methods for four-dimensional CT scan are provided. The methods may include determining a first region of a subject and a second region. A movement of the subject may occur within the second region. The methods may further include generating a first image set by performing, based on a first operation parameter corresponding to a first scan, the first scan on the first region of the subject, and generating a second image set by performing, based on a second operation parameter corresponding to a second scan, the second scan on a second region of the subject. The methods may further include obtaining movement information corresponding to the movement of the subject and determining a final image set based on the first image set, the movement information, and the second image set.

20 Claims, 8 Drawing Sheets

(56) References Cited

U.S. PATENT DOCUMENTS

| | | |
|---|---|---|
| 2006/0291615 A1 | 12/2006 | Nishide et al. |
| 2008/0081991 A1 | 4/2008 | West et al. |
| 2008/0107229 A1 | 5/2008 | Thomas et al. |
| 2011/0150173 A1 | 6/2011 | Shinno |
| 2013/0035588 A1 | 2/2013 | Shea et al. |
| 2014/0148684 A1 | 5/2014 | Foo et al. |
| 2014/0159724 A1 | 6/2014 | Praveen et al. |
| 2015/0272532 A1 | 10/2015 | Allmendinger |
| 2016/0106382 A1 | 4/2016 | Lu et al. |
| 2016/0361569 A1 | 12/2016 | Sayeed |
| 2017/0258432 A1 | 9/2017 | Choi et al. |
| 2019/0035118 A1 | 1/2019 | Zhao et al. |

FOREIGN PATENT DOCUMENTS

| | | |
|---|---|---|
| CN | 106526532 A | 3/2017 |
| CN | 107240140 A | 10/2017 |
| CN | 109009193 A | 12/2018 |
| CN | 109833055 A | 6/2019 |
| DE | 102015224179 A1 | 1/2017 |
| FR | 2889750 A1 | 2/2007 |
| WO | 2018087049 A1 | 5/2018 |

OTHER PUBLICATIONS

Written Opinion in PCT/CN2019/102719 mailed on May 29, 2020, 4 pages.

\* cited by examiner

SYSTEMS AND METHODS FOR FOUR-DIMENSIONAL CT SCAN

CROSS-REFERENCE TO RELATED APPLICATIONS

This application is a continuation of International Application No. PCT/CN2019/102719, filed on Aug. 27, 2019, the entire contents of which are incorporated herein by reference.

TECHNICAL FIELD

The present disclosure generally relates to imaging technology, and more particularly, relates to systems and methods for performing a four-dimensional (4D) scan on a region of a subject using reduced time and/or a reduced radiation dose received by the subject.

BACKGROUND

Imaging technology has been widely used for clinical examination and medical diagnosis. An imaging device may perform one or more scans on a region of interest (ROI) of a subject. For example, the ROI may include the chest, the abdomen, the head, an arm, a leg, or the like, or a portion thereof, or a combination thereof. In some cases, a cyclical movement may occur in the ROI of the subject, such as a cardiac movement, a respiratory movement, an artery pulsation, etc. As a result, the position and/or the volume of a target region (e.g., including a tumor) may change periodically due to the cyclical movement. A 4D scan may be performed on the ROI to identify the position and/or the volume of the target region corresponding to different phases of the cyclic movement. In some cases, the ROI may include many regions, such as the head, the neck, the chest, and the abdomen of a subject. A traditional imaging device, such as a computed tomography (CT) scanner, may be unable to continuously perform the 4D scan for a long period of time due to factors including, e.g., the limitation of heat capacity of a tube of the CT scanner. Additionally, the subject may receive a relatively high radiation dose during the 4D scan. Therefore, it is desirable to provide systems and methods for performing a 4D scan on a region of a subject using reduced time and/or a reduced radiation dose.

SUMMARY

According to an aspect of the present disclosure, a method is provided. The method may be implemented on at least one machine each of which has at least one processor and a storage device. The method may include determining a first region of a subject and a second region. A movement of the subject may occur within the second region. The method may further include generating a first image set by performing, based on a first operation parameter corresponding to a first scan, the first scan on the first region of the subject, and generating a second image set by performing, based on a second operation parameter corresponding to a second scan, the second scan on a second region of the subject. The method may further include obtaining movement information corresponding to the movement of the subject and determining a final image set based on the first image set, the movement information, and the second image set.

In some embodiments, the first scan may be a helical computed tomography scan and the second scan may be a four-dimensional computed tomography scan.

In some embodiments, the first operation parameter may include a first pitch corresponding to the first scan, and the second operation parameter may include a second pitch corresponding to the second scan.

In some embodiments, the first pitch may be larger than the second pitch.

In some embodiments, the method may further include determining, based on the movement of the subject, the second operation parameter.

In some embodiments, the determining a first region of a subject and a second region may include determining, based on a topogram of the subject, at least one of the first region or the second region.

In some embodiments, the movement of the subject may be a physiological movement.

In some embodiments, the obtaining movement information corresponding to the movement of the subject may include determining, via a sensor monitoring the physiological movement during the second scan, the movement information.

In some embodiments, the obtaining movement information corresponding to the movement of the subject may include determining, based on the second image set, the movement information.

In some embodiments, the movement information may include a movement curve depicting the movement of the subject as a function of time.

In some embodiments, the first scan and the second scan may be performed in a single scan.

In some embodiments, the first scan and the second scan may be performed as separate scans.

In some embodiments, the obtaining movement information corresponding to the movement of the subject may include obtaining the movement information corresponding to movement of only the second region of the subject.

In some embodiments, the movement information may exclude information related to a movement that occurs in the first region of the subject.

According to another aspect of the present disclosure, a system is provided. The system may include at least one storage medium storing a set of instructions and at least one processor configured to communicate with the at least one storage medium. When executing the set of instructions, the at least one processor may be directed to cause the system to determine a first region of a subject and a second region and generate a first image set by performing, based on a first operation parameter corresponding to a first scan, the first scan on the first region of the subject. A movement of the subject may occur within the second region. The at least one processor may be further directed to cause the system to generate a second image set by performing, based on a second operation parameter corresponding to a second scan, the second scan on a second region of the subject. The at least one processor may be further directed to cause the system to obtain movement information corresponding to the movement of the subject and determine a final image set based on the first image set, the movement information, and the second image set.

According to yet another aspect of the present disclosure, another system is provided. The system may include a region determination module configured to determine a first region of a subject and a second region. A movement of the subject may occur within the second region. The system may further include an image reconstruction module configured to generate a first image set by performing, based on a first operation parameter corresponding to a first scan, the first scan on the first region of the subject. The image reconstruction module may be further configured to generate a second image set by performing, based on a second operation parameter corresponding to a second scan, the second scan on a second region of the subject. The system may further include an obtaining module, configured to obtain movement information corresponding to the movement of the subject. The system may further include a final image determination module, configured to determine a final image set based on the first image set, the movement information, and the second image set.

According to still another aspect of the present disclosure, a non-transitory computer readable medium is provided. The non-transitory computer readable medium may include at least one set of instructions. When executed by at least one processor of a computer device, the at least one set of instructions may direct the at least one processor to determine a first region of a subject and a second region and generate a first image set by performing, based on a first operation parameter corresponding to a first scan, the first scan on the first region of the subject. A movement of the subject may occur within the second region. The at least one set of instructions may further direct the at least one processor to generate a second image set by performing, based on a second operation parameter corresponding to a second scan, the second scan on a second region of the subject. The at least one set of instructions may further direct the at least one processor to obtain movement information corresponding to the movement of the subject and determine a final image set based on the first image set, the movement information, and the second image set.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
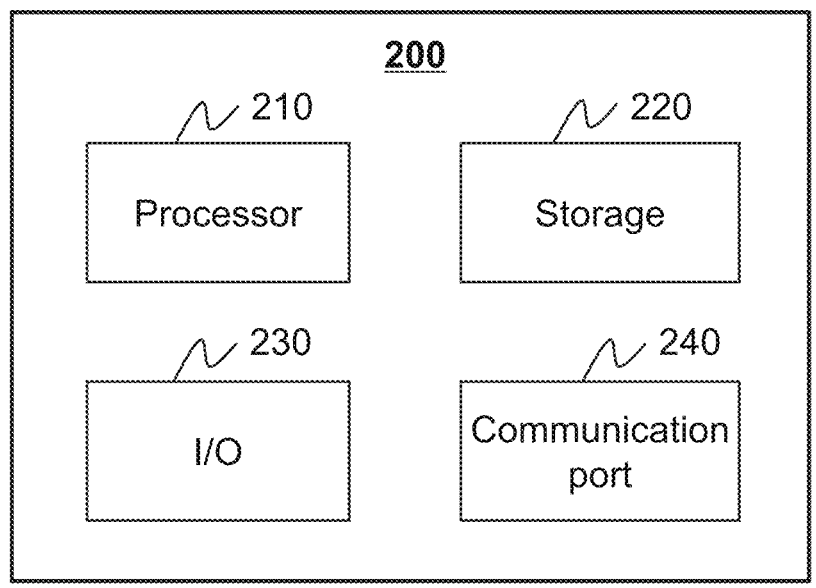
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

As used herein, a portion of an image may be referred to using the name of the body part corresponding to the portion of the image. For example, a liver may refer to a real liver or the representation of a liver in an image. Segmenting an organ or tissue from an image means that segmenting a portion of the image representing the organ or tissue from the image.

Provided herein are systems and components for an imaging system. In some embodiments, the imaging system may include a single modality imaging system and/or a multi-modality imaging system. The single modality imaging system may include, for example, an X-ray imaging system, a computed tomography (CT) system, a magnetic resonance imaging (MRI) system, an ultrasonography system, a positron emission tomography (PET) system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a digital subtraction angiography-magnetic resonance imaging (DSA-MRI) system, etc. It should be noted that the imaging system described below is merely provided for illustration purposes, and not intended to limit the scope of the present disclosure.

The present disclosure provides mechanisms (which can include methods, systems, computer-readable medium, etc.) for performing a four-dimensional (4D) scan on a region of a subject using reduced time and/or a reduced radiation dose received by the subject. Specifically, an imaging device may perform a scan on a region of interest (ROI) of a subject. The ROI may include a first region and a second region. A cyclic movement (e.g., a cardiac movement, a respiratory movement) may occur within the second region of the subject. An imaging device may perform a first scan on a first region of the subject and perform a second scan on a second region of the subject based on different scan or operation parameters, taking into consideration that the cyclic movement occurring in the second region. For example, the first scan may be a three-dimensional (3D) scan, and the second scan may be a 4D scan. In some cases, the first scan and the second scan may both be a helical scan. Operation parameters associated with the first scan may include a first pitch. Operation parameters associated with the second scan may include a second pitch. The first pitch may be greater than the second pitch. The scan on the first region with little or no impact of the cyclic movement occurring in the second region may be faster than the scan on the second region. By performing the 4D scan in only part of the ROI, the scan may be completed with reduced time, which in turn may reduce the radiation dose applied to the subject during the scan if radiation is involved in the scan. A first image set may be determined based on a first set of scan data associated with the first scan. A second image set may be determined based on a second set of scan data associated with the second scan. Movement information (e.g., a movement curve) associated with the movement of the subject may be obtained during the second scan, for example, using one or more sensors. A final image set may be determined based on the first image set, the second image set, and the movement information. For example, one or more second images in the second image set may be assigned to different phases of the movement of the subject. A first image from the first image set may be stitched with a second image from the second image set to generate a final image in the final image set. The final image may be assigned to a phase of the movement of the subject that corresponds to the second image.

Figure 1:
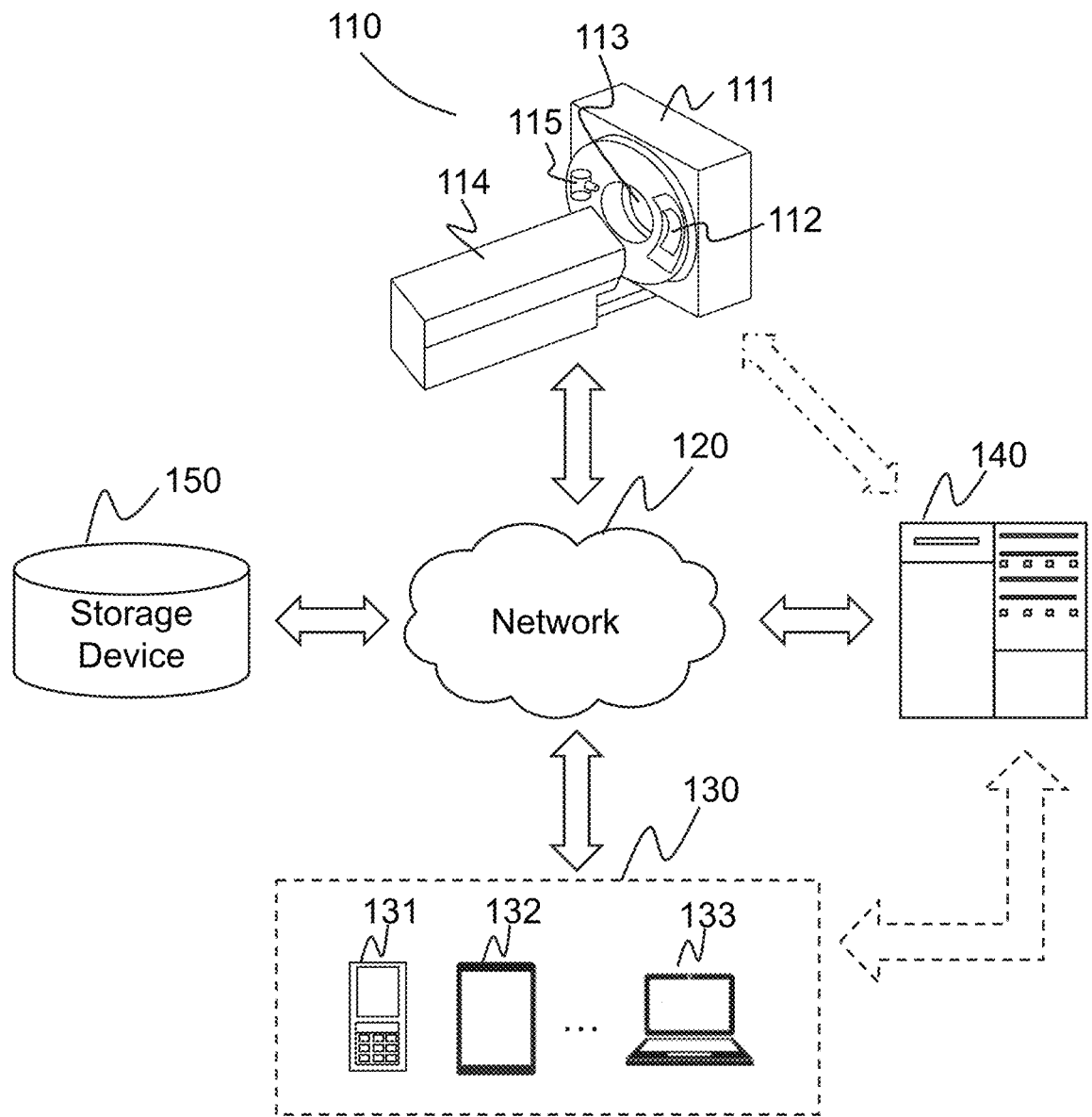
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include an imaging device 110, a network 120, one or more terminals 130, a processing device 140, and a storage device 150. In some embodiments, the imaging device 110, the terminal(s) 130, the processing device 140, and/or the storage device 150 may be connected to and/or communicate with each other via a wireless connection (e.g., the network 120), a wired connection, or a combination thereof. The connection between the components of the imaging system 100 may be variable. Merely by way of example, the imaging device 110 may be connected to the processing device 140 through the network 120, as illustrated in FIG. 1. As another example, the imaging device 110 may be connected to the processing device 140 directly. As a further example, the storage device 150 may be connected to the processing device 140 through the network 120, as illustrated in FIG. 1, or connected to the processing device 140 directly. As still a further example, a terminal 130 may be connected to the processing device 140 through the network 120, as illustrated in FIG. 1, or connected to the processing device 140 directly.

The imaging device 110 may generate or provide image data via scanning a subject (e.g., a patient) disposed on a scanning table of the imaging device 110. In some embodiments, the imaging device 110 may include a single-modality scanner and/or multi-modality scanner. The single-modality scanner may include, for example, a computed tomography (CT) scanner. The multi-modality scanner may include a single photon emission computed tomography-computed tomography (SPECT-CT) scanner, a positron emission tomography-computed tomography (PET-CT) scanner, a computed tomography-ultra-sonic (CT-US) scanner, a digital subtraction angiography-computed tomography (DSA-CT) scanner, or the like, or a combination thereof. In some embodiments, the image data may include projection data, images relating to the subject, etc. The projection data may be raw data generated by the imaging device 110 by scanning the subject, or data generated by a forward projection on an image relating to the subject. In some embodiments, the subject may include a body, a substance, an object, or the like, or a combination thereof. In some embodiments, the subject may include a specific portion of a body, such as a head, a thorax, an abdomen, or the like, or a combination thereof. In some embodiments, the subject may include a specific organ or region of interest, such as an esophagus, a trachea, a bronchus, a stomach, a gallbladder, a small intestine, a colon, a bladder, a ureter, a uterus, a fallopian tube, etc.

In some embodiments, the imaging device 110 may include a gantry 111, a detector 112, a detecting region 113, a couch 114, and a radiation scanning source 115. The gantry 111 may support the detector 112 and the radiation source 115. A subject may be placed on the couch 114 to be scanned. The radiation scanning source 115 may emit radiation rays to the subject. The radiation may include a particle ray, a photon ray, or the like, or a combination thereof. In some embodiments, the radiation may include a plurality of radiation particles (e.g., neutrons, protons, electron, p-mesons, heavy ions), a plurality of radiation photons (e.g., X-ray, a y-ray, ultraviolet, laser), or the like, or a combination thereof. The detector 112 may detect radiations and/or radiation events (e.g., gamma photons) emitted from the detecting region 113. In some embodiments, the detector 112 may include a plurality of detector units. The detector units may include a scintillation detector (e.g., a cesium iodide detector) or a gas detector. The detector unit may be a single-row detector or a multi-row detector.

In some embodiments, the system 100 may further include one or more other devices that may facilitate the scanning of the subject, such as a sensor for detecting movement information of a cyclic movement that occurs within a region of the subject. The cyclic movement may be a physiological movement that occurs periodically, such as a cardiac movement, a respiratory movement, an artery pulsation, a gastrointestinal movement, or the like, or any combination thereof. For example, the sensor for monitoring the respiratory movement may include a camera, a chest belt, and/or an abdomen belt. Merely by way of example, an optical marker may be placed on a region (e.g., the chest and/or the abdomen) of the subject where the cyclic movement occurs, the camera may take one or more images of the optical marker so that movement information related to the region of the subject may be obtained. As another example, the sensor for monitoring the cardiac movement may include one or more electrodes for monitoring electro-cardio signals associated with the subject.

The network 120 may include any suitable network that can facilitate exchange of information and/or data for the imaging system 100. In some embodiments, one or more components of the imaging system 100 (e.g., the imaging device 110, the processing device 140, the storage device 150, the terminal(s) 130) may communicate information and/or data with one or more other components of the imaging system 100 via the network 120. For example, the processing device 140 may obtain image data from the imaging device 110 via the network 120. As another example, the processing device 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may be connected to and/or communicate with the imaging device 110, the processing device 140, and/or the storage device 150. For example, the terminal(s) 130 may obtain a processed image from the processing device 140. As another example, the terminal(s) 130 may obtain image data acquired via the imaging device 110 and transmit the image data to the processing device 140 to be processed. In some embodiments, the terminal(s) 130 may include a mobile device 131, a tablet computer 132, a laptop computer 133, or the like, or any combination thereof. For example, the mobile device 131 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 130 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 140 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 130 may be part of the processing device 140.

The processing device 140 may process data and/or information obtained from the imaging device 110, the storage device 150, the terminal(s) 130, or other components of the imaging system 100. For example, the processing device 140 may reconstruct an image based on projection data generated by the imaging device 110. As another example, the processing device 140 may determine the position of a target region (e.g., a region in a patient) to be scanned by the imaging device 110. As yet another example, the processing device 140 may generate one or more final images by composing an image associated with the first scan on a first region and an image associated with a second scan on a second region. In some embodiments, the processing device 140 may be a single server or a server group. The server group may be centralized or distributed. In some embodiments, the processing device 140 may be local to or remote from the imaging system 100. For example, the processing device 140 may access information and/or data from the imaging device 110, the storage device 150, and/or the terminal(s) 130 via the network 120. As another example, the processing device 140 may be directly connected to the imaging device 110, the terminal(s) 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by a computing device 200 having one or more components as described in connection with FIG. 2.

The storage device 150 may store data, instructions, and/or any other information. In some embodiments, the storage device 150 may store data obtained from the imaging device 110, the processing device 140, and/or the terminal(s) 130. In some embodiments, the storage device 150 may store data and/or instructions that the processing device 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the imaging system 100 (e.g., the processing device 140, the terminal(s) 130). One or more components of the imaging system 100 may access the data or instructions stored in the storage device 150 via the network 120. In some embodiments, the storage device 150 may be part of the processing device 140.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as, public cloud, private cloud, community, and hybrid clouds, etc. However, those variations and modifications do not depart the scope of the present disclosure.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the imaging device 110, the terminals 130, the storage device 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operation s A and B).

The storage 220 may store data/information obtained from the imaging device 110, the terminals 130, the storage device 150, and/or any other component of the imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining the position of a target region of a subject (e.g., a target portion of a patient).

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the imaging device 110, the terminals 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
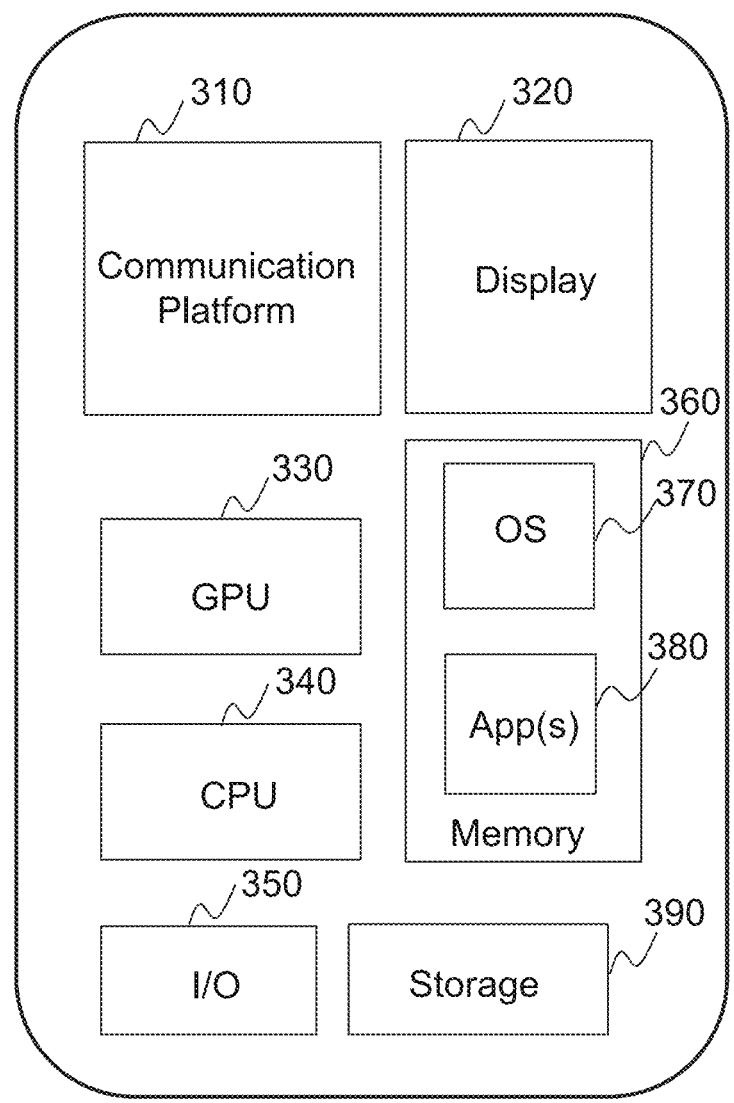
FIG. 3 is a schematic diagram illustrating exemplary hardware and/or software components of an exemplary terminal device according to some embodiments of the present disclosure.

FIG. 3 is a schematic diagram illustrating exemplary hardware and/or software components of an exemplary terminal device 300 on which the terminals 130 may be implemented according to some embodiments of the present disclosure. As illustrated in FIG. 3, the terminal device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the terminal device 300. In some embodiments, a mobile operating system 370 (e.g., iOS™, Android™ Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
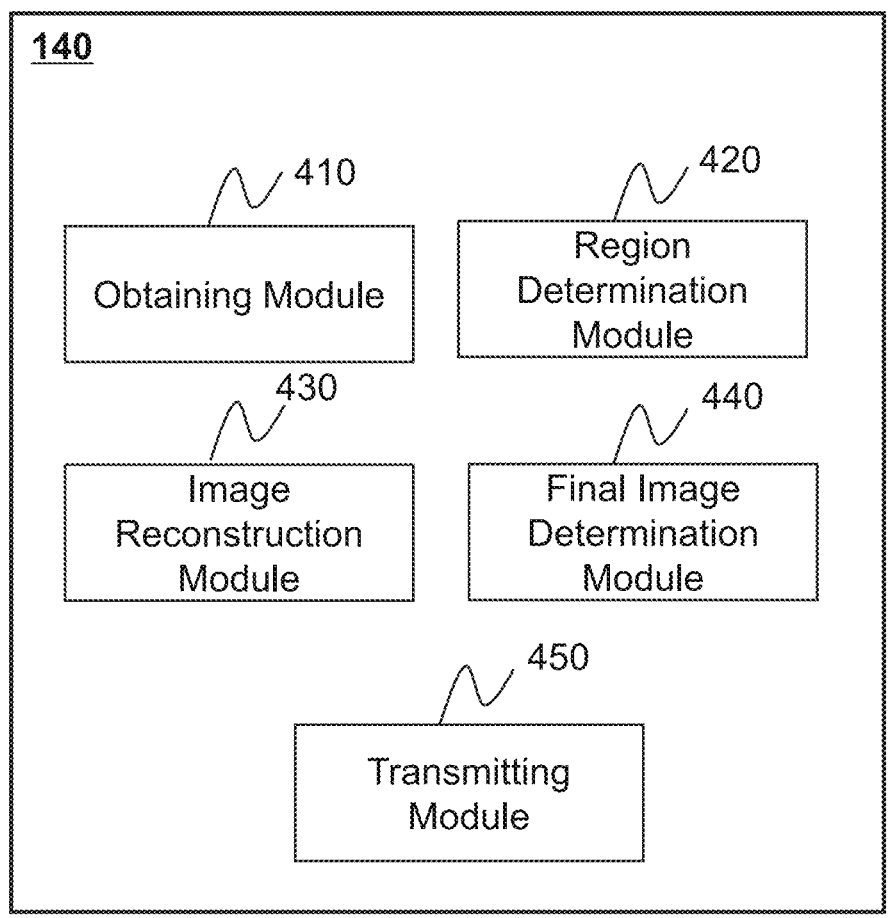
FIG. 4 is a block diagram illustrating an exemplary processing engine according to some embodiments of the present disclosure.

FIG. 4 is a block diagram illustrating an exemplary processing device 140 according to some embodiments of the present disclosure. As illustrated in FIG. 4, the processing device 140 may include an obtaining module 410, a region determination module 420, an image reconstruction module 430, a final image determination module 440, and a transmission module 450. The modules may be hardware circuits of all or part of the processing device 140. The modules may also be implemented as an application or set of instructions read and executed by the processing device 140. Further, the modules may be any combination of the hardware circuits and the application/instructions. For example, the modules may be the part of the processing device 140 when the processing device 140 is executing the application/set of instructions.

The obtaining module 410 may obtain data related to and/or from the imaging system 100. In some embodiments, the obtaining module 410 may obtain a topogram of a subject. The topogram may be generated by a pre-scan on the subject. The topogram may be used to determine a region of interest (ROI) to be scanned by an imaging device (e.g., the imaging device 110 in FIG. 1), a radiation dose to be delivered to the ROI, or the like, or a combination thereof. The ROI may include a first region and a second region. In some embodiments, little or no movement may occur within the first region during a first scan on the first region. In some embodiments, the movement (e.g., a cyclical movement) may occur within the second region. As used herein, the cyclical movement may refer to movement (e.g., physiological movement) of one or more body parts of the subject that occurs periodically. For example, the second region may include at least a portion of the chest and/or at least a portion of the abdomen, and the cyclic movement at issue may include the cardiac movement, the respiratory movement, etc. Specifically, the second region may include but not limited to the heart, a lung, a rib, the stomach, the intestine, or the like, or a portion thereof, or any combination thereof, of the subject. In some embodiments, the obtaining module 410 may obtain a first set of scan data associated with the first scan and a second set of scan data associated with the second scan. In some embodiments, the obtaining module 410 may obtain movement information corresponding to a movement of the subject. In some embodiments, a sensor may be configured to detect movement information (i.e., monitor the movement) corresponding to the cardiac movement or the respiratory movement. In some embodiments, the obtaining module 410 may obtain a movement curve for depicting the cardiac movement or the respiratory movement as a function of time. For example, the movement curve may be an electrocardiogram for depicting the cardiac movement. The electrocardiogram may be a graph of voltage versus time and may show one or more cardiac cycles. As another example, the movement curve may be a breathing curve (as will be described in FIG. 7).

The region determination module 420 may determine the first region and the second region of the subject. For example, the region determination module 420 may automatically determine the one or more first regions and/or the one or more second regions in the topogram. Merely by way of example, the processing device 140 may use an image segmentation technique to segment the one or more first regions and/or the one or more second regions in the topogram. For instance, the processing device 140 may segment the topogram into one or more parts corresponding to one or more organs (and/or different types of tissue) of the subject, such as the head, the heart, the lungs, etc. The processing device 140 may further determine the first region and the second region based on one or more segmented parts including the one or more organs to be scanned, respectively. Exemplary image segmentation techniques may include a threshold-based segmentation technique, a histogram-based technique, a technique using a trained segmentation model, etc. In some embodiments, the user may manually determine the one or more first regions and/or the one or more second regions in the topogram.

The image reconstruction module 430 may reconstruct one or more images. In some embodiments, the image reconstruction module 430 may generate a first image set based on the first set of scan data, and a second image set based on the second set of scan data. Both of the first image set and the second image set may include one or more reconstructed images. For example, the one or more reconstructed images may include one or more two-dimensional (2D) images. The image reconstruction module 430 may reconstruct the one or more 2D images using an iterative algorithm, a filtered back projection (FBP) algorithm, a Radon transform algorithm, a direct Fourier algorithm, or the like, or any combination thereof. As another example, the one or more reconstructed images may include one or more 3D images. The image reconstruction module 430 may reconstruct the one or more 3D images using a multi-planar reconstruction (MPR) algorithm, a maximum intensity projection (MIP) algorithm, a surface shaded display (SSD) algorithm, a volume rendering (VR) algorithm, or the like, or any combination thereof. In some embodiments, each of the plurality of reconstructed images in the second image set may be labelled so that the movement information may be assigned to each of the plurality of reconstructed images. For instance, each of the plurality of reconstructed images may be labelled by a couch position and/or a time point (e.g., a middle time point of a period of time) associated with the acquisition of the scan data corresponding to the reconstructed image.

The final image determination module 440 may determine a final image set including one or more final images. Each of the one or more final images may include the one or more first regions and the one or more second regions. The final image determination module 440 may determine the final image set based on the first image set, the movement information, and the second image set. In some embodiments, the final image determination module 440 may determine the movement information corresponding to the cardiac movement and/or the respiratory movement based on data measured by the sensor that monitors the movement of the subject. In some embodiments, the final image determination module 440 may determine a movement curve for depicting the cardiac movement or the respiratory movement as a function of time. For example, the movement may be divided into ten phases based on the movement curve (e.g., the magnitude of the movement), including a 0% phase, a 10% phase, a 20% phase, a 30% phase, a 40% phase, a 50% phase, a 60% phase, a 70% phase, a 80% phase, and a 90% phase. In some embodiments, the final image determination module 440 may divide the scan data into a plurality of subsets of scan data corresponding to different phases of the movement of the subject. In some embodiments, the final image determination module 440 may assign images reconstructed from the second set of scan data (also referred to as second images) to various phases of a movement cycle, for example, based on labelled couch positions and/or time points associated with the acquisition of the scan data corresponding to the images.

For example, the final image determination module 440 may generate one or more final images by stitching a first image (e.g., a 3D image) from the first image set with one or more second images (e.g., a 3D image) in different image subsets of the second image set. Each of the final images may include both the first region and the second region. The one or more final images may be assigned to one or more phases of the movement of the subject that correspond to the one or more second images. Merely by way of example, an imaging stitching algorithm for generating the one or more final images may include a feature detection process, a feature matching process, an image alignment process, and a compositing process, etc.

The transmission module 450 may send information and/or an instruction to one or more components of the imaging system 100. In some embodiments, the transmission module 450 may transmit the one or more final images in the final image set to a storage device (e.g., the storage device 150) for storage. In some embodiments, the transmission module 450 may transmit the one or more final images in the final image set to a terminal device (e.g., the user terminal 130). A user (e.g., a doctor) may view the one or more final images via a user terminal (e.g., the user terminal 130). For example, the user may view the one or more final images one by one. As another example, the user may send an instruction to the user terminal to cause the user terminal to sequentially display each of the one or more final images on a screen, which may look similar to an animation that shows the movement within the second region.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, any module mentioned above may be divided into two or more units. For example, the image reconstruction module 430 may be divided into two units, one of which may be configured to reconstruct one or more first images from the first set of scan data and one or more second images from the second set of scan data, and the other one may be configured to stitch a first image with a second image to generate a final image. In some embodiments, the processing device 140 may include one or more additional modules. For example, the processing device 140 may further include a control module configured to generate control signals for one or more components in the imaging system 100.

Figure 5:
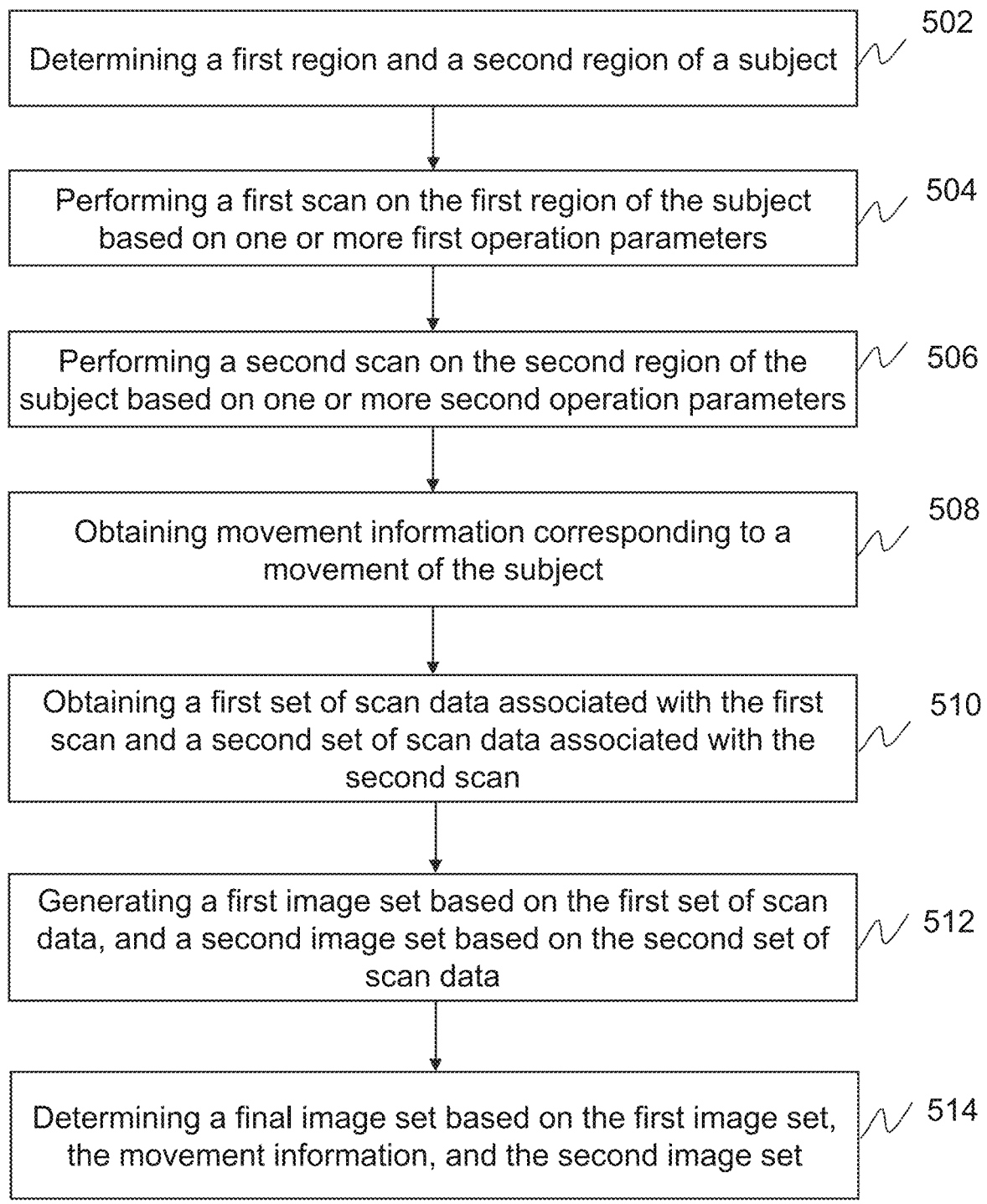
FIG. 5 is a flowchart illustrating an exemplary process for determining a final image set based on a first scan and a second scan of a subject according to some embodiments of the present disclosure.

FIG. 5 is a flowchart illustrating an exemplary process for determining a final image set based on a first scan and a second scan of a subject according to some embodiments of the present disclosure. At least a portion of process 500 may be implemented on the computing device 200 as illustrated in FIG. 2 or the terminal device 300 as illustrated in FIG. 3. In some embodiments, one or more operations of the process 500 may be implemented in the imaging system 100 as illustrated in FIG. 1. In some embodiments, one or more operations in the process 500 may be stored in a storage device (e.g., the storage device 150 and/or the storage 220) in the form of instructions, and invoked and/or executed by the imaging device 110 (e.g., the processing device 140, or the processor 210 of the computing device 200). In some embodiments, the instructions may be transmitted in the form of electronic current or electrical signals. In some embodiments, a portion of the operations in the process 500 may be performed by the processing device 140, and a portion of the operations in the process 500 may be performed by the imaging device 110. The imaging device 110 may perform a CT scan, a PET scan, a SPECT scan, an MRI scan, or the like, or a combination thereof, on a subject, which is within the scope of the present disclosure.

In 502, a user (e.g., an operator) or the processing device 140 (e.g., the region determination module 420) may determine a first region and a second region of a subject. In some embodiments, the subject may include a human, an animal, a mechanical component, or the like, or a combination thereof. In some embodiments, the subject may include a specific portion of a body. A region of interest (ROI) to be scanned by an imaging device (e.g., the imaging device 110 in FIG. 1) may include the first region and the second region. In some embodiments, little or no movement may occur within the first region during a first scan on the first region. As used herein, a region of the subject may be deemed to undergo little or no movement during an imaging process (e.g., a scan) if the region remains still, or any movement of or within the region brings about little or no impact on the scanning (e.g., the movement is too slow and/or the magnitude of the movement is too small to affect the imaging process), or the cyclic movement of another region of the subject asserts little or no impact on the imaging of the region of the subject. For instance, the movement may include a physiological movement such as a respiratory movement, a cardiac movement, an artery pulsation, a gastrointestinal movement, or the like, or any combination thereof. The first region may include but not limited to the head, the neck, a shoulder, a hand, an arm, the pelvis, a leg, a foot, or the like, or a portion thereof, or any combination thereof, of the subject. In some embodiments, the movement (e.g., a cyclical movement) may occur within the second region. As used herein, the cyclical movement may refer to a movement of one or more body parts of the subject that occurs periodically. For example, the second region may include at least a portion of the chest and/or at least a portion of the abdomen, and the cyclic movement at issue may include the cardiac movement, the respiratory movement, etc. Specifically, the second region may include but not limited to the heart, a lung, a rib, the stomach, the intestine, or the like, or a portion thereof, or any combination thereof, of the subject.

In some embodiments, the processing device 140 may obtain a topogram (also referred to as a "scout image") of the subject. The topogram may include one or more first regions and/or one or more second regions. The topogram may be obtained based on a pre-scan of the subject. The topogram may be used to determine the position and the size of the first region and/or the second region. For example, the pre-scan may be a CT scan, a PET-CT scan, an MRI scan, etc. In some embodiments, the pre-scan and the subsequent scan (e.g., the first scan and/or the second scan) performed on the subject may be of the same type (e.g., the CT scan). In some embodiments, the pre-scan and the subsequent scan may be of different types. A region of the subject on which the pre-scan is performed may be determined such that the topogram includes the first region(s) and the second region(s). In some embodiments, the topogram may be a 2D image. In some embodiments, the topogram including one or more first regions and one or more second regions may be obtained by one pre-scan. In some embodiments, a first topogram corresponding to the first region may be obtained based on a first pre-scan on at least a portion of the subject including the first region, and a second topogram corresponding to the second region may be obtained based on a second pre-scan on at least a portion of the subject including the second region.

In some embodiments, the processing device 140 may automatically determine the one or more first regions and/or the one or more second regions in the topogram. Merely by way of example, the processing device 140 may use an image segmentation technique to segment the one or more first regions and/or the one or more second regions in the topogram. For instance, the image segmentation technique may include a threshold-based segmentation technique, a histogram-based technique, a technique using a trained segmentation model, etc. In some embodiments, if the type of the pre-scan is different from the type of the subsequent scan, the processing device 140 may adjust the first region(s) and second region(s) segmented from the topogram so that the first region(s) and the second region(s) are suitable for the subsequent scan. In some embodiments, the user may manually determine the one or more first regions and/or the one or more second regions in the topogram. For example, the user may view the topogram via a terminal device (e.g., the user terminal 130) and mark the one or more first regions and/or the one or more second regions.

In 504, the imaging device 110 may perform a first scan on the first region of the subject based on one or more first operation parameters. In some embodiments, the first scan may be a three-dimensional (3D) scan. Merely by way of example, the first scan may be a CT scan. For instance, the 3D scan may include a helical CT scan or a non-helical CT scan. Specifically, the helical CT scan may include a single-slice helical CT scan or a multi-slice helical CT scan. During the helical CT scan, the couch 114 may move continuously (e.g., along a longitudinal direction of the couch 114) while the gantry rotates around the subject. The one or more first operation parameters corresponding to the helical CT scan of the first region may include but not limited to a tubular voltage, a tubular current, a dose, a scanning field of view (SFOV), a moving speed of the couch 114, a rotation speed of the gantry 111, a pitch, thickness of a slice, or the like, or any combination thereof. The pitch may be associated with a distance travelled by the couch 114 in one round of gantry rotation. As used herein, the pitch corresponding to the first scan is also referred to as a first pitch. The non-helical CT scan may include a CT scan using parallel beams, a CT scan using cone beams, a CT scan using fan beams, etc. The one or more first operation parameters corresponding to the non-spiral CT scan on the first region may include but not limited to a tubular voltage, a tubular current, a dose, a scanning field of view (SFOV), a rotation speed of the gantry 111, a thickness of a slice, or the like, or any combination thereof. In some embodiments, the non-helical CT scan may include a cine scan. During the cine scan, the imaging device 110 may continuously scan an ROI (e.g., the first region) of the subject at a couch position for a certain period of time (also referred to as a cine duration). Then, the radiation source may stop emitting radiation beams and the couch may be moved (e.g., by a predetermined distance) to a next couch position. The imaging device 110 may continuously scan the ROI for the same period of time at the next couch position. As used herein, the cine duration corresponding to the first scan may be referred to as a first cine duration. A first set of scan data may be generated by performing the first scan on the first region.

In 506, the imaging device 110 may perform a second scan on the second region of the subject based on one or more second operation parameters. In some embodiments, the second scan may be a four-dimensional (4D) scan. For instance, the 4D scan may include a helical scan or a cine scan. The 4D scan may be performed by over-sampling data related to the second region at various couch positions. Thus, the data related to the second region may span a portion of a cycle of the movement (e.g., a respiratory cycle, a cardiac cycle), an entire cycle of the movement, or a plurality of cycles of the movement.

In some embodiments, the first scan and the second scan may be performed in a single scan. That is, the first scan and the second scan may be considered as different stages (or portions or sub-scans) of the same scan. Merely by way of example, after the first scan is performed on the first region according to the one or more first operation parameters, the one or more first operation parameters may be changed into the one or more second operation parameters. Then the second scan may be performed on the second scan according to the one or more second operation parameters. In some embodiments, at least a portion of the operation parameters of the first scan and the second scan, both constituting part of a same scan, may be different. In some embodiments, the first scan and the second scan may be separately performed as separate scans. It may be difficult and uncomfortable for a subject (e.g., a child, an infant, or an animal) to hold the same posture during the first scan and the second scan. After the first scan is performed on the first region, there may be a time interval before the second scan commences. In some embodiments, the subject (e.g., a child, an infant) may have a rest during the time interval. After the time interval, the second scan may be performed on the second region after repositioning the subject. In some embodiments, if the first scan and the second scan are performed as separate scans, the first region may partially overlap the second region. In some embodiments, the imaging data of the overlapping region where the first region and the second region overlap may facilitate one or more image processing operations including, e.g., registration of an image (e.g., a topogram) of the first region with an image (e.g., a topogram) of the second region, stitching of an image (e.g., a reconstructed image) of the first region with an image (e.g., a reconstructed image) of the second region, or the like, or a combination thereof. In some embodiments, the first scan and the second scan may be performed in a single scan, and the first region does not have to overlap the second region, which may reduce the radiation dose applied to the subject or a portion thereof.

In some embodiments, at least one of the one or more first operation parameters may be different from a corresponding second operation parameter. For example, the first pitch may be larger than the second pitch, and/or the first cine duration may be shorter than the second cine duration. In some embodiments, the second pitch may be determined based on the movement of the subject. For instance, the second pitch may be determined based on the duration of a movement cycle of the movement in the second region of the subject. As a result, the time period for scanning the second region at each couch position may be longer than the time period for scanning the first region at each couch position. In some embodiments, the second pitch and/or the second cine duration may be determined based on a duration of the cycle of the movement within the second region. Merely by way of example, the second cine duration may be set to be an average duration of the respiratory cycle plus an additional second to account for variations in the respiratory cycle. The average duration of the respiratory cycle may be a default value (e.g., an average duration of respiration of a plurality of patients). Alternatively, the average duration of the respiratory cycle may be associated with the subject (e.g., a specific patient). For instance, a plurality of cycles of the respiratory movement of the subject may be detected by a sensor when the subject breathes freely. The average duration of the respiratory cycle may be determined based on the plurality of cycles detected by the sensor. In some embodiments, the movement of the second region may be non-cyclic. Techniques for monitoring the movement of the subject may be found elsewhere in the present disclosure. See, for example, the description in connection with operation 508. More descriptions regarding the determination of the second pitch may be found, for example, in FIG. 8 and the descriptions thereof. A second set of scan data may be generated by performing the second scan on the second region.

In 508, the processing device 140 (e.g., the obtaining module 410) may obtain movement information corresponding to a movement of the subject during the second scan. In some embodiments, the processing device 140 may obtain the movement information corresponding to movement of only the second region of the subject. In some embodiments, a slight movement (e.g., a cell movement, a molecular movement) may occur in the first region of the subject, and the movement information obtained in operation 508 may exclude information related to the slight movement that occurs in the first region. In some embodiments, a sensor may be configured to detect movement information (i.e., monitor the movement) corresponding to the physiological movement that occurs periodically, such as the cardiac movement, the respiratory movement, the artery pulsation, and the gastrointestinal movement. The cardiac movement may include relaxation and contraction of cardiac muscles, which may result in heartbeats and periodical change of the ventricular volume of the heart. For example, the sensor may monitor the cardiac movement by monitoring electro-cardio signals associated with the subject. Such a sensor may include but not limited to one or more electrodes. The one or more electrodes may be placed over the skin of the subject and may record the electrical activity of the heart of the subject over a period of time. The respiratory movement may include relaxation and contraction of muscles of respiration, which results in inhalation and exhalation, and periodical change of the thoracic cavity. The sensor that monitors the respiratory movement may include an optical sensor (e.g., a camera), a strain gauge, a spirometer, or the like, or any combination thereof. For example, the optical sensor may acquire one or more images to detect an optical marker placed on the chest and/or abdomen when the subject lies on the couch 114. As another example, the strain gauge (e.g., a chest belt and/or an abdomen belt) may be placed on the chest and/or abdomen of the subject, so as to monitor the position change of the chest and/or the abdomen of the subject. In some embodiments, the sensor may monitor the movement information during the second scan so that the movement information may be synchronized with the scan data corresponding to the second scan (also referred to as a second set of scan data). In some embodiments, the operation 508 may be performed after the operation 512. Specifically, the movement information may be determined from reconstructed images corresponding to the second scan (e.g., by a cone-beam CT scanner). For instance, the movement information of the respiratory movement may be determined based on the variations of the anterior surface of the thorax identified from the reconstructed images. In this case, the sensor for detecting the movement information corresponding to the movement of the subject during the second scan may be omitted.

In some embodiments, data measured by the sensor that monitors the movement of the subject may be transmitted to the processing device 140 (e.g., the region determination module 420), and the processing device 140 may determine the movement information corresponding to the cardiac movement and/or the respiratory movement. In some embodiments, the movement information may be determined by an external device and may be obtained by the processing device 140 (e.g., the obtaining module 410). In some embodiments, a movement curve may be generated to depict the cardiac movement or the respiratory movement as a function of time. For example, the movement curve may be an electrocardiogram for depicting the cardiac movement. The electrocardiogram may be a graph of voltage versus time and may show one or more cardiac cycles. As another example, the movement curve may be a breathing curve (as will be described in FIG. 7).

In 510, the processing device 140 (e.g., the obtaining module 410) may obtain a first set of scan data associated with the first scan and a second set of scan data associated with the second scan. For example, the first set of scan data and the second set of scan data may be preliminary projection data of the first region and the second region, respectively. In some embodiments, the processing device 140 may obtain the first set of scan data and/or the second set of scan data from the imaging device 110. In some embodiments, the processing device 140 may obtain the first set of scan data and/or the second set of scan data from a storage (e.g., the storage device 150). In some embodiments, the first set of scan data and/or the second set of scan data may be preprocessed. The preprocessing may eliminate or reduce the influence of some physical factors (e.g., detector gain, beam hardening) on the preliminary projection values. For instance, the preprocessing may include air correction, crosstalk correction, off-focal correction, beam hardening correction, or the like, or any combination thereof.

In 512, the processing device 140 (e.g., the image reconstruction module 430) may generate a first image set based on the first set of scan data, and a second image set based on the second set of scan data. Both of the first image set and the second image set may include one or more reconstructed images. For example, the one or more reconstructed images may include one or more two-dimensional (2D) images reconstructed using an iterative algorithm, a filtered back projection (FBP) algorithm, a Radon transform algorithm, a direct Fourier algorithm, or the like, or any combination thereof. As another example, the one or more reconstructed images may include one or more 3D images reconstructed using a multi-planar reconstruction (MPR) algorithm, a maximum intensity projection (MIP) algorithm, a surface shaded display (SSD) algorithm, a volume rendering (VR) algorithm, or the like, or any combination thereof. In some embodiments, each of the plurality of reconstructed images in the second image set may be labelled so that the movement information may be assigned to each of the plurality of reconstructed images. For instance, each of the plurality of reconstructed images may be labelled by a couch position and/or a time point (e.g., a middle time point of a period of time) associated with the acquisition of the scan data corresponding to the reconstructed image.

In 514, the processing device 140 (e.g., the final image determination module 440) may determine a final image set based on the first image set, the movement information, and the second image set. In some embodiments, the second image set may be divided into a plurality of image subsets based on the movement information. For example, the movement may be divided into ten phases based on the movement curve (e.g., the magnitude of the movement), including a 0% phase, a 10% phase, a 20% phase, a 30% phase, a 40% phase, a 50% phase, a 60% phase, a 70% phase, a 80% phase, and a 90% phase. Merely by way of example, for a respiratory cycle, the 0% phase may correspond to a phase where the magnitude of the movement is zero (e.g., the inhalation has just started). The magnitude of the movement may gradually increase from the 0% phase to the 50% phase. The 50% phase may correspond to a phase where the magnitude of the movement reaches a maximum value in the respiration cycle (e.g., the exhalation has just started). The magnitude of the movement may gradually decrease from the 50% phase to the end of the respiratory cycle. The magnitude of the movement corresponding to the 90% phase may be a relatively small value close to zero. Alternatively, the movement may be divided into four phases, including a 0% phase, a 25% phase, a 50% phase, a 75% phase, etc. As yet another example, the cardiac movement may be divided to a P wave phase, a QRS complex phase, and a T wave phase, based on the electrocardiogram of the heart of the subject. The P wave phase may represent the depolarization of the atria, the QRS complex phase may represent the depolarization of the ventricles, and the T wave phase may represent the repolarization of the ventricles. In some embodiments, the processing device 140 may generate the plurality of image subsets by assigning one or more images in the second image set to one of the various phases of the movement, for example, based on the labelled couch position and/or time point associated with the acquisition of the scan data corresponding to the image(s). Each image subset may correspond to a phase of the movement. In some embodiments, the second set of scan data may be divided into a plurality of subsets of scan data corresponding to different phases of the movement of the subject in operation 510. The plurality of image subsets may be generated in operation 512 by reconstructing one or more images based on the plurality of subset of scan data.

In some embodiments, the final image set may include one or more final images. The processing device 140 may generate one or more final images by stitching a first image (e.g., a 3D image) from the first image set with one or more second images (e.g., a 3D image) in different image subsets of the second image set. Each of the one or more final images may include both the first region and the second region. The one or more final images may be assigned to one or more phases of the movement of the subject that correspond to the one or more second images. Merely by way of example, an imaging stitching algorithm for generating the one or more final images may include a feature detection process, a feature matching process, an image alignment process, and a compositing process, etc. The feature detection process may be configured to extract features in the first image and the second image, which may reflect the correspondence between the first image and the second image. For example, the feature detection process may be performed using a speeded up robust feature (SURF) descriptor, a scale-invariant feature transform (SIFT) feature descriptor, etc. The feature matching process may be performed to match similar features in the images to be stitched so that the images to be stitched may be aligned in the image alignment process. The compositing process may be performed to compose the aligned images into a final image. Performing a normal 3D scan on a first region and a 4D scan on a second region may reduce the time needed to perform the scan on the ROI and reduce the radiation dose received by the subject, as compared to a traditional method including performing a 4D scan on both the first and the second region.

In some embodiments, the one or more final images may be transmitted to the storage device 150 for storage. In some embodiments, the one or more final images may be used for diagnostic purposes. A user (e.g., a doctor) may view the one or more final images via a user terminal (e.g., the user terminal 130). For example, the user may view the one or more final images one by one. As another example, the user may send an instruction to the user terminal to sequentially display each of the one or more final images on a screen, which may look similar to an animation that shows the movement within the second region. In some embodiments, the one or more final images may be used in planning a 4D radiation treatment. A plurality of parameters related to the 4D radiation treatment may be determined based on the movement of a target region (e.g., a tumor in the second region) indicated by the one or more final images to generate a plan for the 4D radiation treatment. In some embodiments, a plan for a 4D radiation treatment may include three-dimensional spatial information and temporal information for the delivery of a radiation dose in the radiation treatment, the operation parameters, control parameters of the radiation source, the gantry, etc., that facilitate to achieve the planned radiation delivery. The control parameters may be determined such that the radiation rays delivered to the subject are adapted to the change of the position and/or size of the target region caused by the movement of the subject within the second region. In the 4D radiation treatment, the radiation rays may be adjusted to adapt to the movement of the target region so that the target region may receive a more accurate dose of radiation and the unnecessary radiation towards the tissue or organ surrounding the target region may be reduced. For instance, the 4D radiation treatment may be a gated radiation treatment. Radiation may be delivered only when the target region is in a position corresponding to a certain phase of movement (e.g., the 0% phase where the inhalation is just started).

It should be noted that the above description regarding the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be omitted and/or one or more additional operations may be added. For example, the process 500 may further include positioning the subject (e.g., a patient) on the couch 114 to perform a pre-scan, generating a topogram of the subject based on data associated with the pre-scan, etc.

Figure 6:
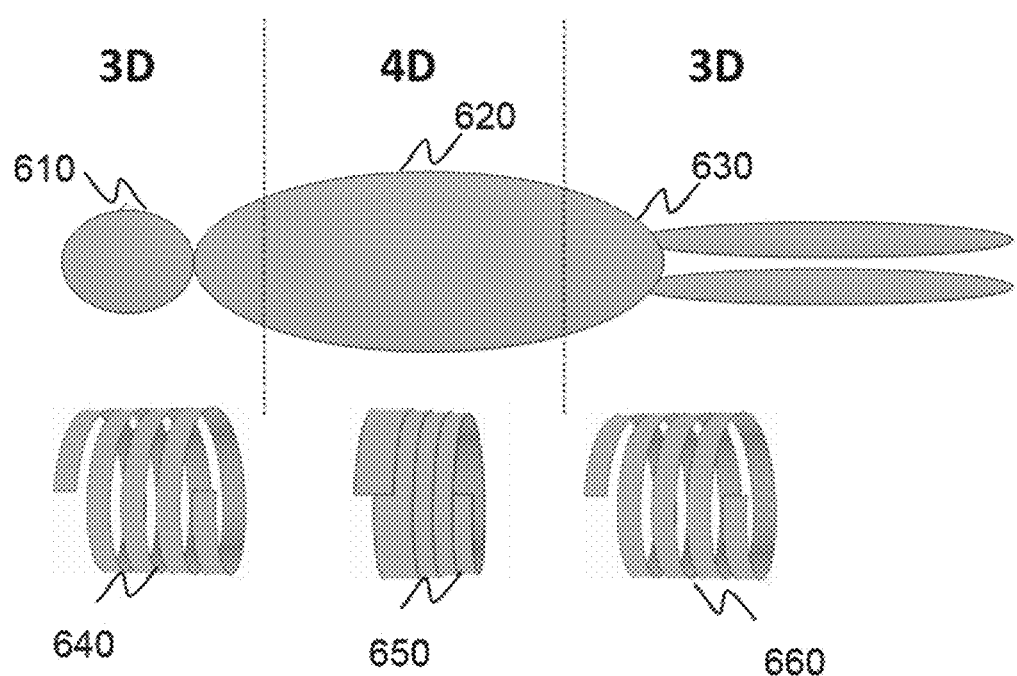
FIG. 6 is a schematic diagram illustrating exemplary first regions and an exemplary second region of the subject according to some embodiments of the present disclosure.

FIG. 6 is a schematic diagram illustrating exemplary first regions and an exemplary second region of the subject according to some embodiments of the present disclosure. As shown in FIG. 6, the subject may be a patient lying on the couch 114 (e.g., in a prone position). A user or the processing device 140 may determine a first region 610, a second region 620, and a third region 630, for example, based on one or more topograms of the subject. A cardiac movement and/or a respiratory movement may occur within the second region 620 of the subject. Little or no movement may occur within the first region 610 and the third region 630. In some embodiments, the third region 630 may be considered as another first region. To obtain a final image including the first region 610, the third region 630, and the second region 620, the imaging device 110 may perform a scan on each of the first region 610, the third region 630, and the second region 620. The first region 610 may include the head, the neck, the shoulder, or the like, or a portion thereof, of the subject. The second region 620 may include the chest and/or the upper abdomen. A movement (e.g., a respiratory movement, a cardiac movement) may occur within the second region 620. The third region 630 may include the lower abdomen, the pelvis, the leg, or the like, or a portion thereof. In some embodiments, the imaging device 110 may perform a single scan on the first region 610, the second region 620, and the third region 630 continuously (e.g., without a time interval and/or repositioning the subject between the scan of the first region, the second region, and the third region). The scan may include three stages, that is, a first scan (e.g., a 3D helical scan) on the first region 610, a second scan (e.g., a 4D helical scan) on the second region, and a third scan (e.g., a 3D helical scan) on the third region. At least a portion of operation parameters for the first scan, the second scan, and the third scan may be different, such as the pitch. In some embodiments, the imaging device 110 may perform three scans on the first region 610, the second region 620, and the third region 630 in any order.

For a helical scan, the couch 114 moves while the gantry 111 rotates around the subject, which makes the radiation rays pass through different positions of the subject. All of the different positions that radiation rays pass through may look like a helical band (e.g., the first helical band 640, the second helical band 650, and the third helical band 660 corresponding to the first region 610, the second region 620, the third region 630, respectively). One or more operations corresponding to a helical scan may include a pitch. In some embodiments, a second pitch corresponding to the second scan may be shorter than a pitch corresponding to the first scan and a pitch corresponding to the third region 630. As illustrated in FIG. 6, a portion of the second helical band 650 may be overlapping with another portion of the second helical band 650. The scan data related to the second region 620 may span a portion of a cycle of the movement (e.g., a respiratory cycle, a cardiac cycle), an entire cycle of the movement, or a plurality of cycles of the movement. Thus, more scan data may be acquired at various positions in the second region 620 of the subject, as compared to the first region 610 and the third region 630.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the first scan may be a cine scan, and the second scan may be a 4D cine scan.

Figure 7:
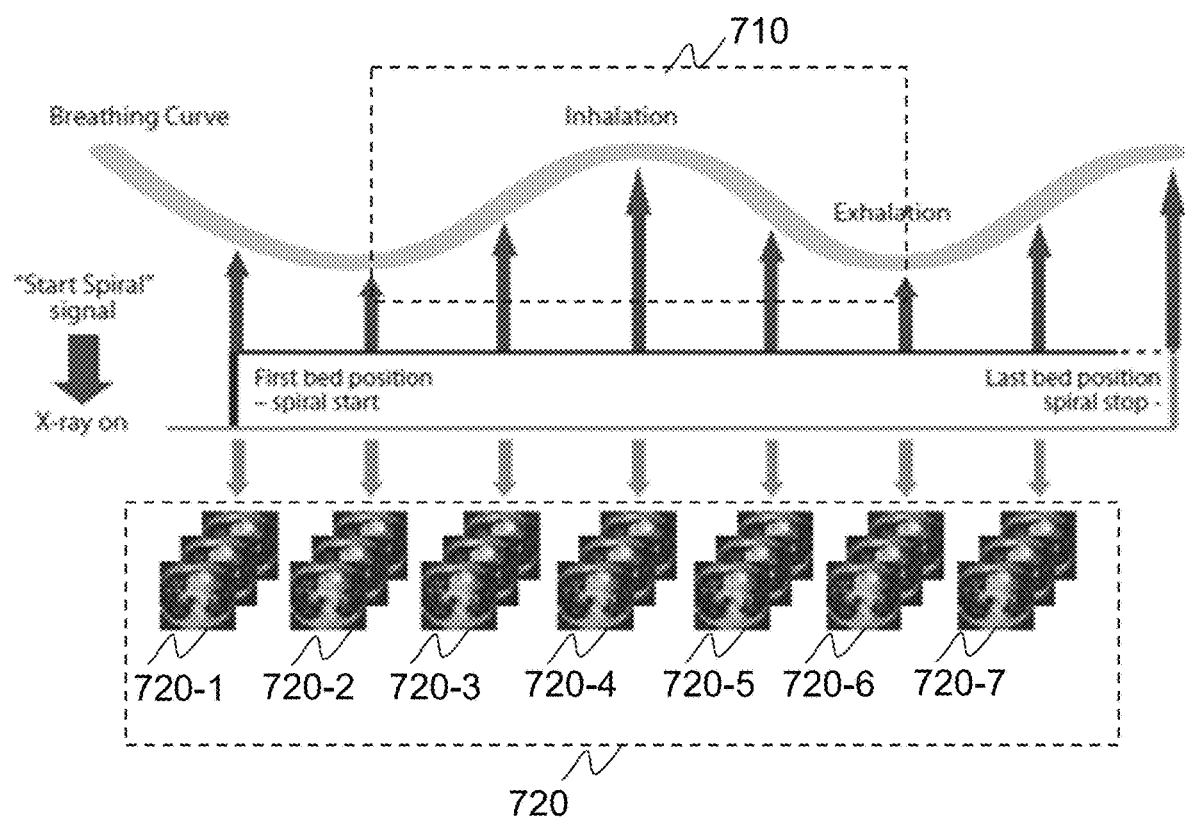
FIG. 7 is a schematic diagram illustrating exemplary image subsets associated with the second region of the subject according to some embodiments of the present disclosure.

FIG. 7 is a schematic diagram illustrating exemplary image subsets associated with the second region of the subject according to some embodiments of the present disclosure. As shown in FIG. 7, the movement information of the respiratory movement may be assigned to a plurality of image subsets 720 of the second image set described in operation 512 and operation 514 in FIG. 5. Merely by way of example, a breathing curve may be used to depict the respiratory movement of the subject as a function of time. Since the couch positions (also referred to as "table positions") at different time points during the scan (e.g., a spiral scan which is also referred to as a helical scan) may be recorded by the imaging system 100, the breathing curve may be transformed to generate a breathing curve depicting the respiratory movement of the subject as a function of the couch position. The processing device 140 may correlate one or more images in the second image set with each phase of the breathing curve based on the labelled couch position and/or time point associated with the acquisition of the scan data corresponding to the one or more images. Merely by way of example, when the processing device 140 sends a "start spiral" signal to the imaging device 110, the radiation source may start emitting radiation rays toward the second region. The image subset 720-1 may correspond to a first couch position where the spiral scan starts. The image subsets 720-2, 720-3, 720-4, and 720-5 may correspond to different phases of the respiratory cycle 710. Specifically, the image subset 720-2 may correspond to a 0% phase, which indicates that a previous exhalation has just ended, and that an inhalation has just started. The image subset 720-3 may correspond to a 25% phase, which is an intermediate phase of the inhalation. The image subset 720-4 may correspond to a 50% phase, which indicates that the inhalation has just ended, and that an exhalation has just started. The image subset 720-5 may correspond to a 75% phase, which is an intermediate phase of the exhalation. The image subset 720-6 may correspond to the end of the respiratory cycle 710 and/or a start of another respiratory cycle (not completely shown in FIG. 7). The image subset 720-7 may correspond to a last couch position where the spiral scan is stopped.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the movement curve may be used to depict a cardiac movement instead of a respiratory movement. As another example, the second scan may be a cine scan.

Figure 8:
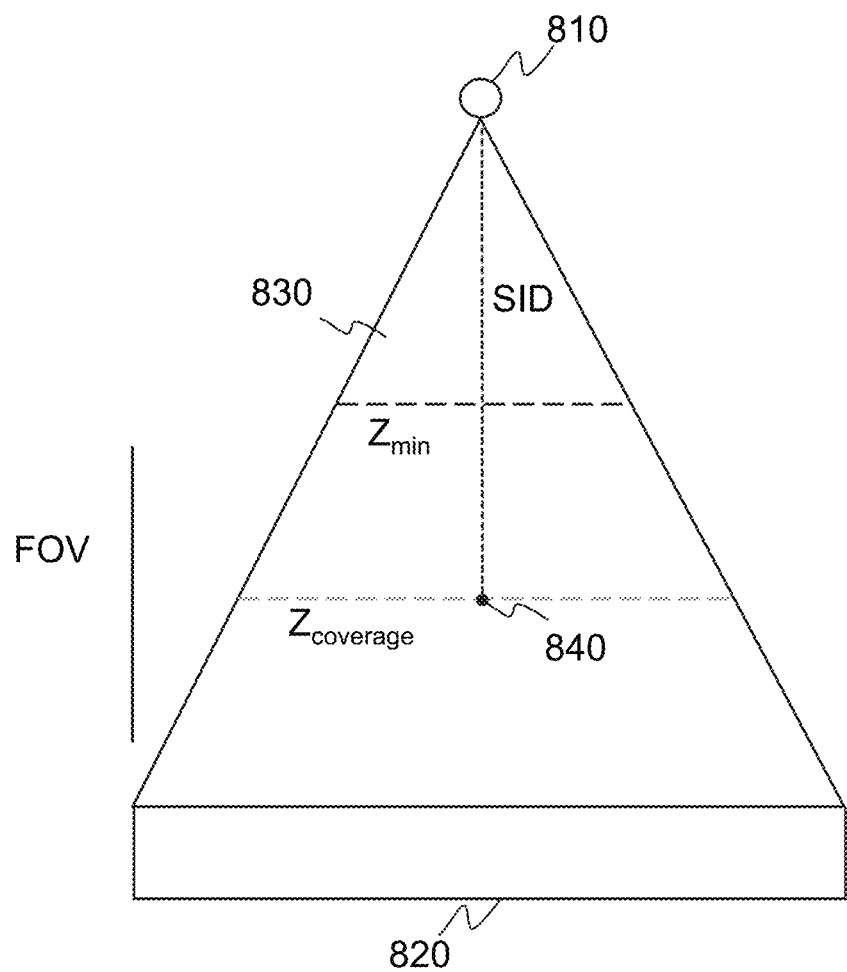
FIG. 8 is a schematic diagram illustrating an exemplary radiation field according to some embodiments of the present disclosure.

FIG. 8 is a schematic diagram illustrating an exemplary radiation field according to some embodiments of the present disclosure. A radioactive scanning source 810 may emit radiation rays toward an ROI (e.g., the first region or the second region). The radiation rays may pass through the ROI and may be received by a detector panel 820. The detector panel 820 may include a plurality of detector elements. The space that the radiation rays passing through may be referred to as a radiation field 830. $Z_{coverage}$ may represent an equivalent width of the detector panel 820 along a rotation axis of the gantry 111 at an isocenter plane. $Z_{min}$ may represent an equivalent width of the detector panel at the upper surface of the ROI. The radiation rays may enter the ROI from the upper surface of the ROI. A source-to-isocenter-distance (SID) may be the distance between the radiation source and an isocenter 840. A field of view (FOV) may be a maximum diameter of the scanned ROI that is represented in the reconstructed image. In some embodiments, the pitch for a helical scan may be determined based on a rotation speed of the gantry 111, a moving speed of the couch 114, and the equivalent width of the detector panel 820 along a rotation axis of the gantry 111 (i.e., $Z_{coverage}$) For example, the pitch may be determined according to the following equation (1):

$$\text{Pitch} = \frac{v_z \times T_R}{Z_{coverage}}, \qquad (1)$$

where $v_z$ represents the moving speed of the couch 114, and $T_R$ represents the rotation duration of the gantry 111. In some embodiments, the pitch for a 4D helical scan may satisfy a condition. For example, the condition may include that the duration of the scan (e.g., the second scan) on the ROI (e.g., the second region) should be the same as or longer than the duration of the movement cycle, such that sufficient scan data may be acquired for reconstructing images corresponding to different phases of the movement cycle. In some embodiments, the pitch may be less than or equal to a parameter associated with the condition. The parameter associated with the condition may be associated with a rotation speed of the gantry 111, the duration of the movement cycle of the subject (e.g., a patient), the FOV, the SID, or the like, or any combination thereof. For instance, a value range of the pitch may be determined according to the following inequation (2).

$$\text{Pitch} \leq \frac{T_R}{T_B} \times \left(1 - \frac{FOV}{2SID}\right), \qquad (2)$$

where $T_B$ represents the duration of a breathing cycle (interchangeably referred to as a "respiratory" cycle) of the subject. Merely by way of example, for a typical 64-array CT scanner, assuming that the FOV is 250 millimeters (mm), the SID is 570 mm, the $Z_{coverage}$ is 30 mm, and $T_R$ is 0.5 seconds (s), $T_B$ is 4 seconds (s), the maximum value of the pitch determined according to the inequation (2) is 0.0936. The moving speed of the couch 114 is determined as 7.488 mm/s. Thus, to perform a 4D helical scan continuously on an ROI including the entire brain and the entire spinal cord, a scanning length may be 1000 mm, and the time needed to complete the 4D helical scan may be about 178 s. Ordinary CT scanners may not be able to continuously perform the helical scan for such a long time. Additionally, the radiation dose for the subject may be relatively high. According to some embodiments of the present disclosure (e.g., described in connection with FIG. 5), the imaging device 110 may perform a first scan (e.g., a normal 3D helical scan) on the first region where no respiratory movement occurs. For example, the first region may include a head, a neck, a shoulder, and the lower abdomen of the subject. For the first scan, assuming that the pitch is 1, the time needed to complete the first scan may be 11 s. According to some embodiments of the present disclosure, the imaging device 110 may perform a second scan (e.g., a 4D helical scan) on a second region where the respiratory movement occurs (e.g., a region including a lung and an upper abdomen). The scanning length for the lung region and the upper abdomen region may be about 350 mm. It may take about 62.3 s to complete the second scan on the second region. As a result, the total time needed to perform the first scan and the second scan on the entire ROI (e.g., including the entire brain and the entire spinal cord) may be 73.3 s, which is significantly lower than the total time need to perform the 4D helical scan on the entire brain and the entire spinal cord (i.e., about 178 s). Additionally, the radiation dose for the subject may also be significantly decreased since the time needed for performing the scan on the ROI is reduced.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A method implemented on at least one machine each of which has at least one processor and a storage device, the method comprising:
  determining a first region of a subject and a second region, wherein a movement of the subject occurs within the second region; and
  generating a final image set by performing a three-dimensional (3D) scan on the first region and a four-dimensional (4D) scan on the second region, comprising:
    generating a first image set by performing, based on a first operation parameter corresponding to the 3D scan, the 3D scan on the first region of the subject;
    generating a second image set by performing, based on a second operation parameter corresponding to the 4D scan, the 4D scan on the second region of the subject;
    obtaining movement information corresponding to the movement of the subject; and,
    determining the final image set based on the first image set, the movement information, and the second image set.

2. The method of claim 1, wherein the 3D scan is a helical computed tomography scan and the 4D scan is a four-dimensional computed tomography scan.

3. The method of claim 1, wherein the first operation parameter includes a first pitch corresponding to the 3D scan, and the second operation parameter includes a second pitch corresponding to the 4D scan.

4. The method of claim 3, wherein the first pitch is larger than the second pitch.

5. The method of claim 1, further comprising:
determining, based on the movement of the subject, the second operation parameter.

6. The method of claim 1, wherein the determining a first region of a subject and a second region comprises:
determining, based on a topogram of the subject, at least one of the first region or the second region.

7. The method of claim 1, wherein the movement of the subject is a physiological movement.

8. The method of claim 7, wherein the obtaining movement information corresponding to the movement of the subject comprises:
determining, via a sensor monitoring the physiological movement during the 4D scan, the movement information.

9. The method of claim 1, wherein the obtaining movement information corresponding to the movement of the subject comprises:
determining, based on the second image set, the movement information.

10. The method of claim 1, wherein the movement information includes a movement curve depicting the movement of the subject as a function of time.

11. The method of claim 1, wherein the 3D scan and the 4D scan are performed in a single scan.

12. The method of claim 1, wherein the 3D scan and the 4D scan are performed as separate scans.

13. The method of claim 1, wherein the obtaining movement information corresponding to the movement of the subject comprises:
obtaining the movement information corresponding to movement of only the second region of the subject.

14. The method of claim 1, wherein the movement information excludes information related to a movement that occurs in the first region of the subject.

15. The method of claim 1, wherein the determining the final image set based on the first image set, the movement information, and the second image set comprises:
dividing the second image set into a plurality of image subsets based on the movement information, wherein each of the plurality of image subsets corresponds to a phase of the movement;
generating one or more final images based on the first image set and one or more second images in different image subsets of the second image set, wherein the one or more final images correspond to one or more phases of the movement of the subject that correspond to the one or more second images.

16. The method of claim 15, wherein the generating one or more final images based on the first image set and one or more second images in different image subsets of the second image set comprises:
generating the one or more final images by stitching a first image from the first image set with the one or more second images in different image subsets of the second image set.

17. The method of claim 11, wherein the first region does not overlap with the second region.

18. The method of claim 12, wherein the first region partially overlaps with the second region.

19. A system, comprising:
at least one storage medium storing a set of instructions; and
at least one processor configured to communicate with the at least one storage medium, wherein when executing the set of instructions, the at least one processor is directed to cause the system to:
determine a first region of a subject and a second region, wherein a movement of the subject occurs within the second region; and
generate a final image set by performing a three-dimensional (3D) scan on the first region and a four-dimensional (4D) scan on the second region, comprising:
generate a first image set by performing, based on a first operation parameter corresponding to the 3D scan, the the 3D on the first region of the subject;
generate a second image set by performing, based on a second operation parameter corresponding to the 4D scan, the 4D scan on the second region of the subject;
obtain movement information corresponding to the movement of the subject; and,
determine the final image set based on the first image set, the movement information, and the second image set.

20. A non-transitory computer readable medium, comprising at least one set of instructions, wherein when executed by at least one processor of a computer device, the at least one set of instructions directs the at least one processor to:
determine a first region of a subject and a second region, wherein a movement of the subject occurs within the second region; and
generate a final image set by performing a three-dimensional (3D) scan on the first region and a four-dimensional (4D) scan on the second region, comprising:
generate a first image set by performing, based on a first operation parameter corresponding to the 3D scan, the 3D scan on the first region of the subject;
generate a second image set by performing, based on a second operation parameter corresponding to the 4D scan, the 4D scan on the second region of the subject;
obtain movement information corresponding to the movement of the subject; and,
determine the final image set based on the first image set, the movement information, and the second image set.

* * * * *